United States Patent
Huh et al.

(10) Patent No.: US 11,351,104 B2
(45) Date of Patent: Jun. 7, 2022

(54) COLLOIDAL DISPERSIONS OF POLY ALPHA-1,3-GLUCAN BASED POLYMERS

(71) Applicant: NUTRITION & BIOSCIENCES USA 4, INC., Rochester, NY (US)

(72) Inventors: Ji Yeon Huh, Newark, DE (US); Natnael Behabtu, Wilmington, DE (US); Rakesh Nambiar, West Chester, PA (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 0 days.

(21) Appl. No.: 15/548,916

(22) PCT Filed: Feb. 2, 2016

(86) PCT No.: PCT/US2016/016136
§ 371 (c)(1),
(2) Date: Aug. 4, 2017

(87) PCT Pub. No.: WO2016/126685
PCT Pub. Date: Aug. 11, 2016

(65) Prior Publication Data
US 2018/0021238 A1    Jan. 25, 2018

Related U.S. Application Data

(60) Provisional application No. 62/112,960, filed on Feb. 6, 2015.

(51) Int. Cl.
| | | |
|---|---|---|
| *A61K 8/73* | (2006.01) | |
| *A61K 8/04* | (2006.01) | |
| *A61Q 5/12* | (2006.01) | |
| *A61Q 15/00* | (2006.01) | |
| *A61Q 19/10* | (2006.01) | |
| *A61Q 19/00* | (2006.01) | |
| *A23L 27/60* | (2016.01) | |
| *C12P 19/04* | (2006.01) | |
| *C12P 19/18* | (2006.01) | |

(52) U.S. Cl.
CPC ............... *A61K 8/73* (2013.01); *A23L 27/60* (2016.08); *A61K 8/04* (2013.01); *A61Q 5/12* (2013.01); *A61Q 15/00* (2013.01); *A61Q 19/00* (2013.01); *A61Q 19/10* (2013.01); *C12P 19/04* (2013.01); *C12P 19/18* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,306,059 A | 12/1981 | Yokobayashi et al. |
| 4,501,886 A | 2/1985 | O'Brien |
| 4,946,700 A | 8/1990 | Taguchi et al. |
| 4,963,298 A | 10/1990 | Allen et al. |
| 5,248,712 A | 9/1993 | Takeuchi et al. |
| 5,296,286 A | 3/1994 | Allen et al. |
| 5,702,942 A | 12/1997 | Leathers et al. |
| 5,712,107 A | 1/1998 | Nichols |
| 5,985,666 A | 11/1999 | Loiselle et al. |
| 6,087,559 A | 7/2000 | Nichols |
| 6,127,602 A | 10/2000 | Nichols |
| 6,127,603 A | 10/2000 | Nichols |
| 6,284,479 B1 | 9/2001 | Nichols |
| 6,410,025 B1 * | 6/2002 | Lander ................ A61K 39/092 424/184.1 |
| 6,465,203 B2 | 10/2002 | Nichols |
| 6,967,027 B1 | 11/2005 | Heux et al. |
| 7,000,000 B1 * | 2/2006 | O'Brien ................ C12P 19/08 536/123.12 |
| 8,076,279 B2 | 12/2011 | Brand et al. |
| 8,197,641 B2 | 6/2012 | Esser et al. |
| 8,551,378 B2 | 10/2013 | Velev et al. |
| 8,642,757 B2 | 2/2014 | O'Brien et al. |
| 8,828,689 B2 | 9/2014 | Caimi et al. |
| 8,835,374 B2 | 9/2014 | Guida et al. |
| 8,871,474 B2 | 10/2014 | Payne et al. |
| 8,962,282 B2 | 2/2015 | Caimi et al. |
| 9,034,092 B2 | 5/2015 | O'Brien |
| 9,080,195 B2 | 7/2015 | O'Brien et al. |
| 9,096,956 B2 | 8/2015 | Shiflett et al. |
| 9,139,718 B2 | 9/2015 | Paullin et al. |
| 9,175,423 B2 | 11/2015 | O'Brien |
| 9,212,301 B2 | 12/2015 | O'Brien et al. |
| 9,278,988 B2 | 3/2016 | Kasat et al. |
| 9,334,584 B2 | 5/2016 | O'Brien et al. |
| 9,365,955 B2 | 6/2016 | Opper |

(Continued)

FOREIGN PATENT DOCUMENTS

| | | |
|---|---|---|
| JP | 11349470 A | 6/1998 |
| JP | 2000159806 A1 | 6/2000 |

(Continued)

OTHER PUBLICATIONS

"Food: Filtration fulfils important role in starch production" by Trevor Sparks, 2012 (Year: 2012).*

(Continued)

*Primary Examiner* — Alton N Pryor

(57) ABSTRACT

A colloidal dispersion is disclosed comprising poly alpha-1,3-glucan or poly alpha-1,3-1,6-glucan and a solvent. The colloidal dispersion has utility in various applications, including food, oil field, pharmaceutical, personal care and specialty industries.

24 Claims, No Drawings

(56) References Cited

U.S. PATENT DOCUMENTS

| | | | |
|---|---|---|---|
| 9,403,917 B2 | 8/2016 | Kasat et al. | |
| 9,540,747 B2 | 1/2017 | O'Brien | |
| 9,562,112 B2 | 2/2017 | Landschutze et al. | |
| 9,644,322 B2 | 5/2017 | Massouda | |
| 9,670,290 B2 | 6/2017 | Landschutze et al. | |
| 9,695,253 B2 * | 7/2017 | Nambiar | C08B 37/0009 |
| 9,701,800 B2 | 7/2017 | Lenzing et al. | |
| 9,708,417 B2 | 7/2017 | Cormier et al. | |
| 9,714,403 B2 | 7/2017 | Nagy et al. | |
| 9,771,548 B2 | 9/2017 | Nagy et al. | |
| 9,957,334 B2 * | 5/2018 | Dennes | A61K 8/73 |
| 9,982,284 B2 | 5/2018 | Nagy et al. | |
| 10,005,850 B2 * | 6/2018 | Kasat | A61K 8/73 |
| 10,030,323 B2 | 7/2018 | Durnberger et al. | |
| 10,072,100 B2 * | 9/2018 | Nambiar | C11D 3/28 |
| 10,087,479 B2 | 10/2018 | Fake et al. | |
| 10,117,937 B2 | 11/2018 | Yao et al. | |
| 2004/0091581 A1 | 5/2004 | Joly et al. | |
| 2005/0059633 A1 | 3/2005 | van Geel-Schuten | |
| 2006/0127328 A1 | 6/2006 | Monsan et al. | |
| 2008/0095731 A1 | 4/2008 | Mitra et al. | |
| 2010/0122378 A1 * | 5/2010 | Frohberg | C08B 37/0009 |
| | | | 800/288 |
| 2011/0014345 A1 | 1/2011 | Pilling | |
| 2011/0189346 A1 * | 8/2011 | Pilling | A23L 1/30 |
| | | | 426/64 |
| 2011/0319310 A1 | 12/2011 | Labeque | |
| 2012/0132381 A1 | 5/2012 | Hentze et al. | |
| 2013/0087938 A1 | 4/2013 | O'Brien et al. | |
| 2013/0157316 A1 | 6/2013 | Caimi et al. | |
| 2013/0161562 A1 | 6/2013 | O'Brien et al. | |
| 2013/0161861 A1 | 6/2013 | O'Brien et al. | |
| 2013/0168895 A1 | 7/2013 | Opper | |
| 2013/0196384 A1 | 8/2013 | Caimi et al. | |
| 2013/0214443 A1 | 8/2013 | Shiflett et al. | |
| 2013/0244287 A1 | 9/2013 | O'Brien et al. | |
| 2013/0244288 A1 | 9/2013 | O'Brien et al. | |
| 2013/0313737 A1 | 11/2013 | O'Brien | |
| 2014/0087431 A1 | 3/2014 | Payne et al. | |
| 2014/0113821 A1 | 4/2014 | Charles et al. | |
| 2014/0179913 A1 | 6/2014 | Paullin et al. | |
| 2014/0187766 A1 | 7/2014 | Kasat et al. | |
| 2014/0187767 A1 | 7/2014 | Kasat et al. | |
| 2014/0323715 A1 | 10/2014 | Kasat et al. | |
| 2015/0080220 A1 * | 3/2015 | Yao | A61K 47/36 |
| | | | 504/358 |
| 2015/0126730 A1 | 5/2015 | O'Brien | |
| 2015/0191550 A1 | 7/2015 | Mishra et al. | |
| 2015/0225877 A1 | 8/2015 | O'Brien | |
| 2015/0232785 A1 | 8/2015 | Paullin et al. | |
| 2015/0240278 A1 | 8/2015 | Nagy et al. | |
| 2015/0299339 A1 | 10/2015 | Shibakami et al. | |
| 2015/0353649 A1 | 12/2015 | Paullin et al. | |
| 2016/0053061 A1 | 2/2016 | Durnberger et al. | |
| 2016/0053406 A1 | 2/2016 | Durnberger et al. | |
| 2016/0060792 A1 | 3/2016 | Durnberger et al. | |
| 2016/0122445 A1 | 5/2016 | Nambiar et al. | |
| 2016/0138195 A1 | 5/2016 | Kraft et al. | |
| 2016/0138196 A1 | 5/2016 | Roder et al. | |
| 2016/0144065 A1 | 5/2016 | Roder et al. | |
| 2016/0175811 A1 | 6/2016 | Behabtu et al. | |
| 2016/0177471 A1 | 6/2016 | Kraft et al. | |
| 2016/0230348 A1 | 8/2016 | Massouda | |
| 2016/0251453 A1 | 9/2016 | Kasat et al. | |
| 2016/0304629 A1 | 10/2016 | Kasat et al. | |
| 2016/0311935 A1 | 10/2016 | Dennes et al. | |
| 2016/0326268 A1 | 11/2016 | Cormier et al. | |
| 2016/0326269 A1 | 11/2016 | Dennes et al. | |
| 2016/0333117 A1 | 11/2016 | Massouda et al. | |
| 2016/0333157 A1 | 11/2016 | Massouda et al. | |
| 2017/0167063 A1 | 6/2017 | Behabtu | |
| 2017/0196231 A1 | 7/2017 | Massouda et al. | |
| 2017/0198108 A1 | 7/2017 | Mishra et al. | |
| 2017/0198109 A1 | 7/2017 | Mishra et al. | |
| 2017/0198322 A1 | 7/2017 | Cheng et al. | |
| 2017/0198323 A1 | 7/2017 | Cheng et al. | |
| 2017/0198324 A1 | 7/2017 | Cheng et al. | |
| 2017/0204203 A1 | 7/2017 | Massouda et al. | |
| 2017/0204232 A1 | 7/2017 | Mishra | |
| 2017/0204442 A1 | 7/2017 | Cheng et al. | |
| 2017/0208823 A1 | 7/2017 | Massouda et al. | |
| 2017/0218093 A1 | 8/2017 | Cheng et al. | |
| 2017/0267787 A1 | 9/2017 | Nambiar et al. | |
| 2017/0298303 A1 | 10/2017 | Nagy et al. | |
| 2017/0362345 A1 | 12/2017 | Behabtu et al. | |
| 2018/0049457 A1 | 2/2018 | Cheng et al. | |
| 2018/0066214 A1 | 3/2018 | Nagy et al. | |
| 2018/0273731 A1 | 9/2018 | Opietnik et al. | |
| 2019/0186049 A1 | 6/2019 | Durnberger et al. | |
| 2019/0218373 A1 | 7/2019 | Opietnik et al. | |

FOREIGN PATENT DOCUMENTS

| | | | |
|---|---|---|---|
| WO | 2005/053765 A1 | 6/2005 | |
| WO | 2006/036092 A1 | 4/2006 | |
| WO | 2013/036918 A2 | 3/2013 | |
| WO | 2013/036968 A1 | 3/2013 | |
| WO | 2013/052730 A1 | 4/2013 | |
| WO | 2013/096502 A1 | 6/2013 | |
| WO | 2013/096511 A1 | 6/2013 | |
| WO | 2013/101854 A1 | 7/2013 | |
| WO | 2013/177348 A1 | 11/2013 | |
| WO | 2014/052386 A2 | 4/2014 | |
| WO | 2014/077340 A1 | 5/2014 | |
| WO | 2014/099724 A1 | 6/2014 | |
| WO | 2014/105696 A1 | 7/2014 | |
| WO | 2014/105698 A1 | 7/2014 | |
| WO | 2014/161018 A1 | 10/2014 | |
| WO | 2014/161019 A1 | 10/2014 | |
| WO | 2014/165881 A1 | 10/2014 | |
| WO | 2014/201479 A1 | 12/2014 | |
| WO | 2014/201480 A1 | 12/2014 | |
| WO | 2014/201481 A1 | 12/2014 | |
| WO | 2014/201482 A1 | 12/2014 | |
| WO | 2014/201483 A1 | 12/2014 | |
| WO | 2014/201484 A1 | 12/2014 | |
| WO | 2015/069828 A1 | 5/2015 | |
| WO | 2015/094402 A1 | 6/2015 | |
| WO | 2015/095046 A1 | 6/2015 | |
| WO | 2015/095358 A1 | 6/2015 | |
| WO | 2015/103531 A1 | 7/2015 | |
| WO | 2015/109064 A1 | 7/2015 | |
| WO | 2015/109066 A1 | 7/2015 | |
| WO | 2015/109164 A1 | 7/2015 | |
| WO | 2015/123323 A1 | 8/2015 | |
| WO | 2015/123327 A1 | 8/2015 | |
| WO | 2015/130881 A1 | 9/2015 | |
| WO | 2015/138283 A1 | 9/2015 | |
| WO | 2015/183721 A1 | 12/2015 | |
| WO | 2015/183724 A1 | 12/2015 | |
| WO | 2015/195777 A1 | 12/2015 | |
| WO | 2015/195960 A1 | 12/2015 | |
| WO | 2015/200589 A1 | 12/2015 | |
| WO | 2015/200590 A1 | 12/2015 | |
| WO | 2015/200593 A1 | 12/2015 | |
| WO | 2015/200596 A1 | 12/2015 | |
| WO | 2015/200605 A1 | 12/2015 | |
| WO | 2015/200612 A1 | 12/2015 | |
| WO | WO 2015183714 A1 | 12/2015 | |
| WO | WO 2015183722 A1 | 12/2015 | |
| WO | WO 2015183726 A1 | 12/2015 | |
| WO | WO 2015183729 A1 | 12/2015 | |
| WO | 2016/073732 A1 | 5/2016 | |
| WO | 2016/105971 A1 | 6/2016 | |
| WO | 2016/106011 A1 | 6/2016 | |
| WO | 2016/106068 A1 | 6/2016 | |

OTHER PUBLICATIONS

Striegel et al., "An SEC/MALS study of alternan degradation during size-exclusion chromatographic analysis", Anal Bioanal Chem 394: 1887-1893 (2009) (Year: 2009).*

(56) References Cited

OTHER PUBLICATIONS

Tanford, C., "Physical Chemistry of Macromolecules", section 18c (1961), John Wiley & Sons (New York) (Year: 1961).*
Simpson et al.(Four glucosyltransferases, GtfJ, Gtfk, GtfL and GtfM, from *Streptococcus salivarius* ATTC 25975, Microbiologgy, 1995, 141, 1451-60). (Year: 1995).*
Simpson et al., "Four glucosyltransferases, Gtfj, GTFK, GtfL and GtfM, from *Streptococcus salivarius* ATCC 25975", Microbiology, vol. 141, 1995, pp. 1451-1460.
PCT International Search Report and Written Opinion for International Application No. PCT/US2016/016136, dated Apr. 4, 2016.
PCT International Search Report and Written Opinion for International Application No. PCT/US2015/066317, dated Mar. 30, 2016.
PCT International Search Report and Written Opinion for International Application No. PCT/US2015/037656, dated Oct. 7, 2015.
PCT International Search Report and Written Opinion for International Application No. PCT/US2015/037646, dated Oct. 7, 2015.
PCT International Search Report and Written Opinion for International Application No. PCT/US2015/037634, dated Sep. 22, 2015.
PCT International Search Report and Written Opinion for International Application No. PCT/US2015/037628, dated Sep. 22, 2015.
PCT International Search Report and Written Opinion for International Application No. PCT/US2015/037624, dated Oct. 12, 2015.
PCT International Search Report and Written Opinion for International Application No. PCT/US2015/037622, dated Sep. 22, 2015.
PCT International Search Report and Written Opinion for International Application No. PCT/US2015/011724, dated May 15, 2015.
PCT International Search Report and Written Opinion for International Application No. PCT/US2015/011551, dated Jul. 9, 2015.
PCT International Search Report and Written Opinion for International Application No. PCT/US2015/011546, dated May 28, 2015.
PCT International Search Report and Written Opinion for International Application No. PCT/US2015/010139, dated Apr. 29, 2015.
PCT International Search Report and Written Opinion for International Application No. PCT/US2014/044281, dated Sep. 11, 2014.
PCT International Search Report and Written Opinion for International Application No. PCT/US2013/076919, dated Mar. 3, 2014.
PCT International Search Report and Written Opinion for International Application No. PCT/US2013/076905, dated Mar. 4, 2014.
Ogawa et al: "Molecular and Crystal Structure of the Regenerated Form of (I–>3)-alpha-d-glucan", International Journal of Biological Macromolecules, vol. 3, No. 1, Feb. 1, 1981, pp. 31-36.
OGAWA et al: "Crystal Structure of (1–>3)-alpha-d-glucan", Water-soluble Polymers: Synthesis, Solution Properties and Applications, American Chemical Society, vol. 141, Jan. 1, 1980, pp. 353-362.
Ogawa et al., 'X-ray Diffraction Data for (I>3)-alpha-d-glucan,' Carbohydrate Research, Oct. 1, 1979, vol. 75, pp. CI3-CI6.
Ogawa et al, "X-ray Diffraction Data for (I–>3)-alpha-d-glucan Triacetate", Carbohydrate Polymers, vol. 3, No. 4, Jan. 1, 1983, pp. 287-297.
International Preliminary Report on Patentability, PCT/US16/16136, Agnes Wittmann Regis, Authorized Officer, IB, dated Aug. 17, 2017.
"Applied Fibre Science", F. Happey, Ed, Chapter 8, Academic Press, New York, 1979 (Book not included).
Behabtu et al., Enzymatic Polymerization Routes to Synthetic-Natural Materials: A Review,ACS Sustainable Chem. Eng., vol. 8, pp. 9947-9954 (2020).

* cited by examiner

COLLOIDAL DISPERSIONS OF POLY ALPHA-1,3-GLUCAN BASED POLYMERS

This application is the National Stage application of International Application No. PCT/US2016/16136 (filed Feb. 2, 2016), which claims the benefit of U.S. Provisional Application No. 62/112,960 (filed Feb. 6, 2015), all of which prior applications are incorporated herein by reference in their entirety.

FIELD OF DISCLOSURE

This disclosure is in the field of colloidal dispersions. Specifically, this disclosure pertains to using poly alpha-1, 3-glucan or poly alpha-1,3-1,6-glucan in colloidal dispersions.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber comprising hexose units, wherein at least 50% of the hexose units within the polymer were linked via alpha-1,3-glycosidic linkages using a *Streptococcus salivarius* gtfJ enzyme. This enzyme utilizes sucrose as a substrate in a polymerization reaction producing poly alpha-1,3-glucan and fructose as end-products (Simpson et al., 1995). The disclosed glucan triacetate polymer formed a liquid crystalline solution when it was dissolved above a critical concentration in a solvent or in a mixture comprising a solvent. From this solution continuous, strong fibers were spun. After regeneration back to glucan cotton-like fibers, highly suitable for use in textiles, were created and used.

Development of new colloidal dispersions are desirable given their potential utility in various applications, including food, oil field, pharmaceutical, personal care and specialty industries.

SUMMARY OF THE DISCLOSURE

In a first embodiment, the disclosure concerns a colloidal dispersion comprising: (a) poly alpha-1,3-glucan or poly alpha-1,3-1,6-glucan; and (b) a solvent.

In a second embodiment, the poly alpha-1,3-1,6-glucan has alpha-1,3 and alpha-1,6-glycosidic linkages comprising: (a) at least 30% of the glycosidic linkages are alpha-1,3 linkages; and (b) at least 30% of the glycosidic linkages are alpha-1,6 linkages.

In a third embodiment, the poly alpha-1,3-glucan and the poly alpha-1,3-1,6-glucan comprise particles with an average particle diameter size of between 5 nm and 200 nm.

In a fourth embodiment, the particles have a spherical or cylindrical shape.

In a fifth embodiment, the particles form aggregates with an average aggregate diameter size of between 10 nm and 200 μm.

In a sixth embodiment, the solvent is water.

In a seventh embodiment, the poly alpha-1,3-glucan or poly alpha-1,3-1,6-glucan constitutes between 0.1% by wt. and 15% by wt. of the total colloidal dispersion.

In an eighth embodiment, the colloidal dispersion has a viscosity of at least 10 cPs.

In a ninth embodiment, the colloidal dispersion has a pH between 1 and 14.

In a tenth embodiment, the colloidal dispersion has a viscosity and a pH wherein the viscosity changes less than 10% while the pH is changed over a range between 2 and 11.

In an eleventh embodiment, the colloidal dispersion further comprises a salt or surfactant wherein the colloidal dispersion has a viscosity that changes less than 10% after the addition of the salt or surfactant.

In a twelfth embodiment, the colloidal dispersion has shear thinning behavior or shear thickening behavior.

In a thirteenth embodiment, the colloidal dispersion is in the form of a personal care product, pharmaceutical product, food product, household product, or industrial product.

In a fourteenth embodiment, the disclosure concerns a personal care product comprising a colloidal dispersion comprising: (a) poly alpha-1,3-glucan or poly alpha-1,3-1,6-glucan; and (b) a solvent.

In a fifteenth embodiment, the disclosure concerns a food product comprising a colloidal dispersion comprising: (a) poly alpha-1,3-glucan or poly alpha-1,3-1,6-glucan; and (b) a solvent.

In a sixteenth embodiment, the disclosure concerns a process for making a poly alpha-1,3-glucan or poly alpha-1,3-1,6-glucan colloidal dispersion comprising: (a) heating an enzyme reaction solution comprising an aqueous basic buffered solution of an enzyme, sucrose and, optionally, antimicrobial agent to make a slurry containing poly alpha-1,3-glucan or poly alpha-1,3-1,6-glucan; (b) filtering the slurry to isolate the poly alpha-1,3-glucan or poly alpha-1, 3-1,6-glucan in the form of a wet cake; (c) washing the wet cake with water; and (d) dispersing the wet cake in water to form a poly alpha-1,3-glucan colloidal dispersion.

In a seventeenth embodiment, the disclosure concerns a process for making a poly alpha-1,3-glucan or poly alpha-1,3-1,6-glucan colloidal dispersion can have at least one of the following: (a) heating the enzyme reaction solution at 20-25° C. for 24 hours; (b) the enzyme for making poly alpha-1,3-glucan is *Streptococcus salivarius* gtfJ; (c) the enzyme for making poly alpha-1,3-1,6-glucan is *Streptococcus oralis* gtf 4297, *Streptococcus* sp. C150 gtf 3298 or *Streptococcus mutans* gtf 0544; (d) the aqueous basic buffered solution has a pH buffering agent of an alkali metal phosphate buffer; (e) the alkali metal phosphate buffer wherein the alkali metal is potassium; (f) the aqueous basic buffered solution has a pH between 7 and 5; (g) the antimicrobial agent is FERMASURE®; and (h) the wet cake contains between 60 to 80% wt % water.

In an eighteenth embodiment, the disclosure concerns a poly alpha-1,3-glucan or poly alpha-1,3-1,6-glucan colloidal dispersion prepared according to a process comprising: (a) heating an enzyme reaction solution comprising an aqueous basic buffered solution of an enzyme, sucrose and, optionally, antimicrobial agent to make a slurry containing poly alpha-1,3-glucan or poly alpha-1,3-1,6-glucan; (b) filtering the slurry to isolate the poly alpha-1,3-glucan or poly alpha-1,3-1,6-glucan in the form of a wet cake; (c) washing the wet cake with water; and (d) dispersing the wet cake in water to form a poly alpha-1,3-glucan colloidal dispersion.

DETAILED DESCRIPTION OF DISCLOSURE

The disclosures of all patent and non-patent literature cited herein are incorporated herein by reference in their entirety.

As used herein, the term "colloidal dispersion" refers to a heterogeneous system having a dispersed phase and a dispersion medium, i.e., microscopically dispersed insoluble particles are suspended throughout another substance. An example of a colloidal dispersion in water is a hydrocolloid. The colloidal dispersion may be a stable colloidal dispersion or an unstable colloidal dispersion. The stable colloidal dispersion is stable at room temperature and/or at elevated temperature, for example, between 40 and 50° C. for a period of at least one month with no visible settling. The unstable dispersion, under the same conditions, may see at least a portion of the poly alpha-1,3-glucan and/or poly alpha-1,3-1,6-glucan settle out of the dispersion. Agitation of the settled material will generally re-form the colloidal dispersion. In some embodiments, the colloidal dispersion is a stable dispersion. In other embodiments, the colloidal dispersion is an unstable dispersion.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least 50% of the glycosidic linkages are alpha-1,3-glycosidic linkages. Poly alpha-1,3-glucan is a type of polysaccharide. The structure of poly alpha-1,3-glucan can be illustrated as follows:

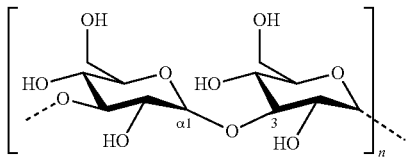

Poly alpha-1,3-glucan can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The terms "poly alpha-1,3-1,6-glucan", "alpha-1,3-1,6-glucan polymer", and "poly (alpha-1,3)(alpha-1,6) glucan" are used interchangeably herein (note that the order of the linkage denotations "1,3" and "1,6" in these terms is of no moment). Poly alpha-1,3-1,6-glucan herein is a polymer comprising glucose monomeric units linked together by glycosidic linkages (i.e., glucosidic linkages), wherein at least 30% of the glycosidic linkages are alpha-1,3-glycosidic linkages, and at least 30% of the glycosidic linkages are alpha-1,6-glycosidic linkages. Poly alpha-1,3-1,6-glucan is a type of polysaccharide containing a mixed glycosidic linkage content. The meaning of the term poly alpha-1,3-1, 6-glucan in certain embodiments herein excludes "alternan," which is a glucan containing alpha-1,3 linkages and alpha-1,6 linkages that consecutively alternate with each other (U.S. Pat. No. 5,702,942, U.S. Pat. Appl. Publ. No. 2006/0127328). Alpha-1,3 and alpha-1,6 linkages that "consecutively alternate" with each other can be visually represented by . . . G-1,3-G-1,6-G-1,3-G-1,6-G-1,3-G-1,6-G-1,3-G- . . . , for example, where G represents glucose.

The percentage of glycosidic linkages between the glucose monomer units of poly alpha-1,3-glucan used to prepare poly alpha-1,3-glucan compounds herein that are alpha-1,3 is at least 50%, 60%, 70%, 80%, 90%, 95%, 96%, 97%, 98%, 99%, or 100% (or any integer value between 50% and 100%). In such embodiments, accordingly, poly alpha-1,3-glucan has less than 50%, 40%, 30%, 20%, 10%, 5%, 4%, 3%, 2%, 1%, or 0% (or any integer value between 0% and 50%) of glycosidic linkages that are not alpha-1,3.

A glucan wet cake is formed from a glucan colloidal dispersion by removing water by filtration. Water remains on the surface of glucan solid particles and trapped between particles. Whereas the glucan colloidal dispersion is a pourable liquid, the wet cake has a soft solid-like consistency.

The term "poly alpha-1,3-glucan slurry" herein refers to an aqueous mixture comprising the components of a glucosyltransferase enzymatic reaction such as poly alpha-1,3-glucan, sucrose, one or more glucosyltransferase enzymes, glucose and fructose.

The term "poly alpha-1,3-glucan wet cake" herein refers to poly alpha-1,3-glucan that has been separated from a slurry and washed with water or an aqueous solution. Poly alpha-1,3-glucan is not dried when preparing a wet cake.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pa-s). A centipoise is one one-hundredth of a poise; one poise is equal to $0.100 \text{ kg·m}^{-1}\text{·s}^{-1}$. Thus, the terms "viscosity modifier" and "viscosity-modifying agent" as used herein refer to anything that can alter/modify the viscosity of a fluid or aqueous composition.

The term "shear thinning behavior" as used herein refers to a decrease in the viscosity of the colloidal dispersion as shear rate increases. The term "shear thickening behavior" as used herein refers to an increase in the viscosity of the colloidal dispersion as shear rate increases. "Shear rate" herein refers to the rate at which a progressive shearing deformation is applied to the colloidal dispersion. A shearing deformation can be applied rotationally.

The "molecular weight" of the poly alpha-1,3-glucan and poly alpha-1,3-glucan compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as high-pressure liquid chromatography (HPLC), size exclusion chromatography (SEC), or gel permeation chromatography (GPC).

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight (% by wt.)", "weight percentage (wt %)" and "weight-weight percentage (% w/w)" are used interchangeably herein. Percent by weight refers to the percentage of a material on a mass basis as it is comprised in a composition, mixture or solution.

Viscosity can be measured with the colloidal dispersion at any temperature between 3° C. to 110° C. (or any integer between 3 and 110° C.). Alternatively, viscosity can be measured at a temperature between 4° C. to 30° C., or 20° C. to 25° C. Viscosity can be measured at atmospheric pressure (about 760 torr) or any other higher or lower pressure.

The viscosity of a colloidal dispersion disclosed herein can be measured using a viscometer or rheometer, or using any other means known in the art. It would be understood by those skilled in the art that a rheometer can be used to measure the viscosity of those hydrocolloids and aqueous solutions of the disclosure that exhibit shear thinning behavior or shear thickening behavior (i.e., liquids with viscosities that vary with flow conditions). The viscosity of such embodiments can be measured at a rotational shear rate of 10 to 1000 rpm (revolutions per minute) (or any integer between 10 and 1000 rpm), for example. Alternatively, viscosity can be measured at a rotational shear rate of 10, 60, 150, 250, or 600 rpm.

The pH of a colloidal dispersion disclosed herein can be between 2.0 to 12.0. Alternatively, pH can be 2.0, 3.0, 4.0, 5.0, 6.0, 7.0, 8.0, 9.0, 10.0, 11.0, 12.0; or between 4.0 to 8.0; or between 3.0 and 11.0. In certain embodiments, the viscosity of the colloidal dispersion does not largely fluctuate at a pH between 3.0 and 11.0.

A poly alpha-1,3-glucan or poly alpha-1,3-1,6-glucan compound disclosed herein can be present in a colloidal dispersion at a weight percentage (wt %) of at least 0.01%, 0.05%, 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5%, 6%, 7%, 8%, 9%, 10%, 11%, 12%, 13%, 14% or 15%.

A colloidal dispersion disclosed herein can be in the form of, and/or comprised in, a personal care product, pharmaceutical product, food product, household product, or industrial product. Poly alpha-1,3-glucan compounds herein can be used as thickening agents in each of these products. Such a thickening agent may be used in conjunction with one or more other types of thickening agents if desired, such as those disclosed in U.S. Pat. No. 8,541,041, the disclosure of which is incorporated herein by reference in its entirety.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient. An active ingredient is generally recognized as an ingredient that causes the intended pharmacological effect.

In certain embodiments, the colloidal dispersion comprising the poly alpha-1,3-glucan and/or the poly alpha-1,3-1,6-glucan can be a skin care product that can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). In addition to the colloidal dispersion, the skin care product may further comprise one or more one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil. In some embodiments, the skin care product comprising the colloidal dispersion can further comprise one or more of an oil, a wax, a fragrance, UV absorber, a pigment, an amino acid, a fatty acid, a dye, an antioxidant, vitamins, retinol, alpha hydroxy acids, salicylic acid or any of the ingredients listed above.

The poly alpha-1,3-glucan and/or the poly alpha-1,3-1,6-glucan can be present in the personal care product in the range of from 0.05 to 15% by weight, based on the total weight of the personal care product composition. In other embodiments, the poly alpha-1,3-glucan and/or the poly alpha-1,3-1,6-glucan can be present in the range of from 0.1 to 10% by weight or from 0.1 to 5% by weight, all percentages by weight are based on the total amount of the personal care product.

In some embodiments, the personal care product comprises or consists essentially of the colloidal dispersion comprising the poly alpha-1,3-glucan and/or the poly alpha-1,3-1,6-glucan, one or more oils, one or more emulsifiers, water and one or more preservatives. In other embodiments, the personal care product comprises or consists essentially of the colloidal dispersion comprising the poly alpha-1,3-glucan and/or the poly alpha-1,3-1,6-glucan, one or more oils, one or more emulsifiers, water, one or more emollients and one or more preservatives. In still further embodiments, the personal care product comprises or consists essentially of the colloidal dispersion comprising the poly alpha-1,3-glucan and/or the poly alpha-1,3-1,6-glucan, one or more oils, one or more emulsifiers, water, one or more emollients, one or more fragrances and one or more preservatives.

A personal care product herein can also be in the form of makeup or other product including, but not limited to, a lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, preshaving product, after-shaving product, cleanser, skin gel, rinse, toothpaste, or mouthwash, for example. In some embodiments, the personal care product comprising the colloidal dispersion can further comprise one or more of an oil, a wax, a fragrance, a UV absorber, UV absorber, a pigment, an amino acid, a fatty acid, a dye, an antioxidant, vitamins, retinol, alpha hydroxy adds, salicylic acid or any of the ingredients listed above.

A pharmaceutical product herein can be in the form of an emulsion, liquid, elixir, gel, suspension, solution, cream, or ointment, for example. Also, a pharmaceutical product herein can be in the form of any of the personal care products disclosed herein. A pharmaceutical product can further comprise one or more pharmaceutically acceptable carriers, diluents, and/or pharmaceutically acceptable salts. A poly alpha-1,3-glucan compound disclosed herein can also be used in capsules, encapsulants, tablet coatings, and as an excipients for medicaments and drugs. In some embodiments, the pharmaceutical product comprising the colloidal dispersion can further comprise one or more of active ingredients, sweeteners, coloring agents, lactose, lecithin, flavoring agents, magnesium oxide, malic acid, benzoic acid, benzyl alcohol, parabens, carbonates, waxes, oils, cellulose, corn starch or a combination thereof. The inactive ingredients that can be part of a pharmaceutical product are carefully controlled by the United States Food and Drug Administration (FDA). Any of those ingredients that are known and recognized by the FDA can be used as a part of the pharmaceutical product.

Non-limiting examples of food products herein include vegetable, meat, and soy patties; reformed seafood; reformed cheese sticks; cream soups; gravies and sauces; salad dressing; mayonnaise; onion rings; jams, jellies, and syrups; pie filling; potato products such as French fries and extruded fries; batters for fried foods, pancakes/waffles and cakes; pet foods; beverages; frozen desserts; ice cream; cultured dairy products such as cottage cheese, yogurt, cheeses, and sour creams; cake icing and glazes; whipped topping; leavened and unleavened baked goods; and the like.

The the colloidal dispersion comprising the poly alpha-1,3-glucan and/or the poly alpha-1,3-1,6-glucan can be used as a filler in the food product or, in other embodiments, can be used as a replacement for at least a portion of an oil or fat in a food product, thus producing a low fat version of the food product.

A non-limiting example of a household product or industrial product is a liquid detergent. The glucan colloidal dispersion can be used as a structuring agent or thickener to stabilize the components in liquid detergent formulation. In some embodiments, the household product comprising the colloidal dispersion can further comprise one or more of alcohols, surfactants, polymers, pigments, dyes, fragrances, enzymes, builders, chealating agents, pH regulators, amines, oils, waxes or combinations thereof. A number of ingredients are known for household products can be used along with the colloidal dispersions. Any of those known ingredients can be used.

The present disclosure is directed toward a colloidal dispersion comprising: (a) poly alpha-1,3-glucan or poly alpha-1,3-1,6-glucan; and (b) a solvent. In some embodiments, the colloidal dispersion consists essentially of (a) poly alpha-1,3-glucan or poly alpha-1,3-1,6-glucan; and (b) a solvent. In other embodiments, the colloidal dispersion comprises less than 1% by weight of sucrose and/or fructose, wherein the percentage by weight is based on the total amount of the colloidal dispersion. The poly alpha-1,3-1,6-glucan has alpha-1,3 and alpha-1,6-glycosidic linkages comprising: (a) at least 30%, 40% or 50% of the glycosidic linkages are alpha-1,3 linkages; and (b) at least 30%, 40% or 50% of the glycosidic linkages are alpha-1,6 linkages.

The poly alpha-1,3-glucan and the poly alpha-1,3-1,6-glucan comprise particles with an average particle diameter size of between 5 nm, 10 nm or 20 nm and 100 nm, 150 nm or 200 nm. Preferably the particles have an average particle diameter size of between 5 nm and 200 nm and more preferably between 10 nm and 100 nm. The particles can have a spherical or cylindrical shape. Typically, the particles are substantially spherical in shape. By substantially is meant that greater than 50% of the particles are spherical in shape. The particles can form aggregates with an average aggregate diameter size of between 10 nm, 100 nm, 1 µm or 10 µm and 100 µm, 150 µm or 300 µm. Preferably the aggregates have an average aggregate diameter size of between 10 nm and 250 µm and more preferably between 10 µm and 225 µm. In all cases, the average size refers to the D50 particle size, or the particle size in which 50% of the particles are larger and 50% of the particles are smaller than the D50 value.

The solvent for the colloidal dispersion can be water. In other embodiments, the solvent can be a combination of water and less than 50% by weight of one or more water-miscible organic solvents, for example, methanol, ethanol, isopropanol, propanol, acetone, ethylene glycol, acetic acid, tetrahydrofuran, dimethyl sulfoxide, dimethyl formamide or a combination thereof, wherein the percentage by weight is based on the total amount of the solvent.

The poly alpha-1,3-glucan characterized by having alpha-1,3-glycosidic linkages or the poly alpha-1,3-1,6-glucan characterized by having alpha-1,3 and alpha-1,6-glycosidic linkages of the colloidal dispersion constitutes between 0.1, 1 or 5% by wt. and 10, 15, 20, 40 or 60% by wt. of the total colloidal dispersion. Preferably the poly alpha-1,3-glucan or poly alpha-1,3-1,6-glucan of the colloidal dispersion constitutes between 0.1% by wt. and 15% by wt. and more preferably between 0.1% by wt. and 10% by wt.

The colloidal dispersion has a viscosity of at least 10, 100, 1,000, 10,000, 100,000 or 1,000,000 cPs.

The colloidal dispersion has a pH between 1 or 2 and 11, 12, 13 or 14. The pH is preferably between 1 and 14 and more preferably between 2 and 11.

The colloidal dispersion has a viscosity and a pH wherein the viscosity changes less than 10, 20, 30, 40 or 50% while the pH is changed over a range between 1 or 2 and 11, 12, 13 or 14. Preferably the viscosity changes less than 50% while the pH changes over a range between 1 and 14 and more preferably the viscosity changes less than 10% while the pH changes over a range between 2 and 11.

The colloidal dispersion can further comprise a salt or surfactant wherein the colloidal dispersion has a viscosity that changes less than 10% after the addition of the salt or surfactant.

The colloidal dispersion has shear thinning behavior or shear thickening behavior.

The colloidal dispersion can be used in the form of a personal care product, pharmaceutical product, food product, household product, or industrial product.

The present disclosure is further directed toward a personal care product comprising a colloidal dispersion comprising: (a) poly alpha-1,3-glucan or poly alpha-1,3-1,6-glucan; and (b) a solvent.

The present disclosure is still further directed toward a food product comprising a colloidal dispersion comprising: (a) poly alpha-1,3-glucan or poly alpha-1,3-1,6-glucan; and (b) a solvent.

The present disclosure is still further directed toward a process for making a poly alpha-1,3-glucan or poly alpha-1,3-1,6-glucan colloidal dispersion comprising: (a) heating an enzyme reaction solution comprising an aqueous basic buffered solution of an enzyme, sucrose and, optionally, antimicrobial agent to make a slurry containing poly alpha-1,3-glucan or poly alpha-1,3-1,6-glucan; (b) filtering the slurry to isolate the poly alpha-1,3-glucan or poly alpha-1,3-1,6-glucan in the form of a wet cake; (c) washing the wet cake with water; and (d) dispersing the wet cake in water to form the poly alpha-1,3-glucan or the poly alpha-1,3-1,6-glucan colloidal dispersion. The process can have at least one of the following: (a) heating the enzyme reaction solution at 20-25° C. for 24 hours; (b) the enzyme for making poly alpha-1,3-glucan is *Streptococcus salivarius* gtfJ; (c) the enzyme for making poly alpha-1,3-1,6-glucan is *Streptococcus oralis* gtf 4297, *Streptococcus* sp. C150 gtf 3298 or *Streptococcus mutans* gtf 0544; (d) the aqueous basic buffered solution has a pH buffering agent of an alkali metal phosphate buffer; (e) the alkali metal phosphate buffer wherein the alkali metal is potassium; (f) the aqueous basic buffered solution has a pH between 7 and 5; (g) the antimicrobial agent is FERMASURE® sodium chlorite; and (h) the wet cake contains between 60 to 80 wt % water.

The present disclosure is still further directed toward a poly alpha-1,3-glucan or poly alpha-1,3-1,6-glucan colloidal dispersion prepared according to a process comprising: (a) heating an enzyme reaction solution comprising an aqueous basic buffered solution of an enzyme, sucrose and, optionally, antimicrobial agent to make a slurry containing poly alpha-1,3-glucan or poly alpha-1,3-1,6-glucan; (b) filtering the slurry to isolate the poly alpha-1,3-glucan or poly alpha-1,3-1,6-glucan in the form of a wet cake; (c) washing the wet cake with water; and (d) dispersing the wet cake in water to form a poly alpha-1,3-glucan colloidal dispersion.

Test Methods

Particle Size Primary particle size was analyzed using a slurry of poly alpha-1,3-glucan with Atomic Force Microscopy (AFM). 10 uL of a slurry of poly alpha-1,3-glucan was placed on a freshly cleaved mica surface, spun at 6000 r/s for 10 seconds, dried at room temperature and imaged by AFM tapping mode. AFM images were obtained using a Dimensional Icon scanning probe Dimensional Icon scanning probe microscope (Bruker, Santa Barbara, Calif.). The microscope was operated in the Tapping Mode, in which the cantilever is oscillated at resonance and the feedback control adjusts for constant tapping amplitude. Typically, tapping mode was used to provide both topographic and phase images. The topography image is a quantitative three-dimensional image of the surface, and the color or brightness of any pixel in the image represents height. Scanning was carried out in air using commercially available 125-/m-long silicon OTESP tips, with 37-55 N/m spring constant, and over 300 kH frequencies with a moderate tapping ratio from 0.85 to 0.65.

Particle Aggregate Size was measured with a Beckman Coulter LS13320 which uses laser diffraction to determine the volume distribution of a field of particles in the range of 0.4 to 2000 um. A standard Fraunhofer regression model was used for the particle size distribution measurements. Three repeat runs are made as a check on sample stability and on instrument reproducibility.

Viscosity was measured by a Brookfield DV3T Rheometer equipped with a recirculating bath to control temperature (20° C.) and a YULA15-E(Z) spindle. The shear rate was increased using a gradient program which increased from 0.01-250 rpm and then shear rate was increased by 7.05 (l/s) every 20 seconds.

pH was measured by VWR symphony H10P.

Determination of Glycosidic Linkages was determined by NMR (nuclear magnetic resonance). Twenty glycosidic linkages in glucan products synthesized by a gtf enzyme were determined by $_{13}$C NMR or $_1$H NMR.

For $_{13}$C NMR, dry glucan polymer (25-30 mg) was dissolved in 1 mL of deuterated DMSO containing 3% by weight of LiCl with stirring at 50° C. Using a glass pipet, 0.8 mL of the solution was transferred into a 5-mm NMR tube. A 25 quantitative $_{13}$C NMR spectrum was acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse-gated decoupling pulse sequence using waltz decoupling was used with an acquisition time of 0.629 second, an inter-pulse delay of 5 seconds, and 6000 30 pulses. The time domain data was transformed using an exponential multiplication of 2.0 Hz.

For $_1$H NMR, approximately 20 mg of a glucan polymer sample was weighed into a vial on an analytical balance. The vial was removed from the balance and 0.8 mL of deuterated DMSO (DMSO-d6), containing 3% by weight of LiCl, was added to the vial. The mixture was stirred with a magnetic stir bar 5 and warmed to 90° C. until the glucan sample dissolved. The solution was allowed to cool to room temperature. While stirring at room temperature, 0.2 mL of a 20% by volume solution of trifluoroacetic acid (TFA) in DMSO-d6 was added to the polymer solution. The TFA was added in order to move all hydroxyl proton signals out of the region of the spectrum where carbohydrate ring proton signals 10 occur. A portion, 0.8 mL, of the final solution was transferred, using a glass pipet, into a 5-mm NMR tube. A quantitative $_1$H NMR spectrum was acquired using an NMR spectrometer with a proton frequency of 500 MHz or greater. The spectrum was acquired using a spectral window of 11.0 ppm and a transmitter offset of 5.5 ppm. A 90° pulse was applied for 32 pulses with an inter-pulse 15 delay of 10 seconds and an acquisition time of 1.5 seconds. The time domain data were transformed using an exponential multiplication of 0.15 Hz.

EXAMPLES

The disclosure is further defined in the following Examples. It should be understood that these Examples, while indicating certain preferred aspects of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various uses and conditions.

Example 1

Preparation of a Colloidal Dispersion Comprising Poly Alpha-1,3-Glucan

U.S. Pat. No. 7,000,000 disclosed a polysaccharide fiber comprising hexose units wherein at least 50% of the hexose units within the polymer were linked via alpha-1,3-glycosidic linkages using a *Streptococcus salivarius* gtfJ enzyme. This enzyme utilizes sucrose as a substrate in a polymerization reaction producing poly alpha-1,3-glucan and fructose as end-products.

A slurry of poly alpha-1,3-glucan was prepared from an aqueous solution (0.5 L) containing *Streptococcus salivarius* gtfJ enzyme (100 unit/L) described in U.S. Patent Appl. Publ. No. 2013/0244288, which is incorporated herein by reference in its entirety, sucrose (100 g/L) obtained from OmniPur Sucrose (EM8550), potassium phosphate buffer (10 mM) obtained from Sigma Aldrich, and FermaSure®, an antimicrobial agent, (100 ppm) obtained from DuPont adjusted to pH 5.5. The resulting enzyme reaction solution was maintained at 20-25° C. for 24 hours. A slurry was formed since the poly alpha-1,3-glucan synthesized in the reaction was aqueous insoluble. The poly alpha-1,3-glucan solids produced in the reaction were collected using a Buchner funnel fitted with a 325-mesh screen over 40 micrometer filter paper, forming the wet cake which contains about 60-80 wt % of water. The poly alpha-1,3-glucan wet cake is then dispersed in water using conventional agitators without high shear, high temperature, long mixing time or separate mixing steps. For example, dispersing in water using an Ika Ultra-Turrax® T25 digital disperser, typically at 8000 rpm for 5 min at ambient temperature.

Example 2a-c

Preparation of Colloidal Dispersions Comprising Poly Alpha-1.3-1,6-Glucan

Poly alpha-1,3-1,6-glucan was made from a slurry of poly alpha-1,3-1,6-glucan. A slurry of poly alpha-1,3-1,6-glucan was prepared from an aqueous solution (0.5 L) containing an enzyme of Streptococcus oralis gtf 4297, Streptococcus sp. C150 gtf 3298 or Streptococcus mutans gtf 0544 for Examples 2a-c, respectively, (100 unit/L) described in U.S. Patent Appl. Publ. No. 2014/0087431, which is incorporated herein by reference in its entirety, sucrose (100 g/L) obtained from OmniPur Sucrose (EM8550), potassium phosphate buffer (50 mM) obtained from Sigma Aldrich, and FermaSure® (100 ppm) obtained from DuPont adjusted to pH 6.5. The resulting enzyme reaction solution was maintained at 22-25° C. for 24-30 hours. A slurry was formed since the poly alpha-1,3-1,6-glucan synthesized in the reaction was aqueous insoluble. The poly alpha-1,3-1,6-glucan solids produced in the reaction were collected using a Buchner funnel fitted with a 325-mesh screen over 40 micrometer filter paper, forming the wet cake which contains about 60-80 wt % of water. The poly alpha-1,3; 1,6-glucan wet cake is then dispersed in water using an Ika Ultra-Turrax® T25 digital disperser, typically at 8000 rpm for 5 min. Different enzymes yielded different ratios of 1,3 to 1,6 glycosidic linkages. Enzyme Streptococcus oralis gtf 4297 produced 31% alpha-1,3 linkages and 67% alpha-1,6 linkages, Streptococcus sp. C150 gtf 3298 produced 50% alpha-1,3 linkages and 50% alpha-1,6 linkages and Streptococcus mutans gtf 0544 produced 62% alpha-1,3 linkages and 36% alpha-1,6 linkages.

Example 3

Primary Particle Size of Glucan

Primary particle size was analyzed using a slurry of poly alpha-1,3-glucan described in Example 1 with Atomic Force Microscopy (AFM). 10 uL of a slurry of poly alpha-1,3-glucan was placed on a freshly cleaved mica surface, spun at 6000 r/s for 10 seconds, dried at room temperature and imaged by AFM tapping mode. AFM images were obtained using a Dimensional Icon scanning probe Dimensional Icon scanning probe microscope (Bruker, Santa Barbara, Calif.). The microscope was operated in the Tapping Mode, in which the cantilever is oscillated at resonance and the feedback control adjusts for constant tapping amplitude. Typically, tapping mode was used to provide both topographic and phase images. The topography image is a quantitative three-dimensional image of the surface, and the color or brightness of any pixel in the image represents height. Scanning was carried out in air using commercially available 125-/m-long silicon OTESP tips, with 37-55 N/m spring constant, and over 300 kH frequencies with a moderate tapping ratio from 0.85 to 0.65. The AFM images indicate that the average diameter of primary particles are 20-30 nm.

Example 4

Particle Size Distribution of Glucan

Particle size distribution was measured using the samples described in Example 1 and Example 2 with a Beckman Coulter LS13320 which uses laser diffraction to determine the volume distribution of a field of particles in the range of 0.4 to 2000 um. A standard Fraunhofer regression model was used for the particle size distribution measurements. Three repeat runs are made as a check on sample stability and on instrument reproducibility. In Table 1, D10, D50 and D90 indicate the diameter of particle or duster at 10%, 50% and 90% in the cumulative distribution, respectively. D50 indicates the median diameter or the medium value of the particle size distribution.

TABLE 1

Particle Size Distribution of Glucan

| Sample | D10 (um) | D50 (um) | D90 (um) |
| --- | --- | --- | --- |
| Poly alpha-1,3-glucan | 5.91 | 12.19 | 29.51 |
| Poly alpha-1,3-1,6 glucan | 50.38 | 213.25 | 374.66 |

Example 5

Particle Shape of Glucan

While most particles have a generally spherical shape, some particles have a cylindrical or rod-like shape. For purposes of measuring size of cylindrical shapes, the diameter is calculated as an effective diameter after the mass of the cylindrical shaped particle is adjusted as if it had a spherical shape.

Example 6

Effect of Shear Rate on the Viscosity of Glucan

To prepare 5 wt % poly alpha-1,3-glucan dispersion, 8.6 g of poly alpha-1,3-glucan wet cake (L6B1C6, 29 wt %) was dispersed in 50 mL of deionized water as described in Example 1. To determine the viscosity of poly alpha-1,3-glucan dispersed in water at various shear rates, the hydrocolloid samples were subjected to various shear rates using a Brookfield DV3T Rheometer equipped with a recirculating bath to control temperature (20° C.) and a YULA15-E(Z) spindle. The shear rate was increased using a gradient program which increased from 0.01-250 rpm and then shear rate was increased by 7.05 (l/s) every 20 seconds. The results summarized in Table 2 indicate that the viscosity of poly alpha-1,3-glucan dispersed in water is reduced as the shear rate is increased. This observation means that the hydrocolloids demonstrate significant shear thinning behavior.

TABLE 2

Effect of Shear Rate on Viscosity of Glucan

| Poly Alpha-1,3-Glucan Loading | Viscosity (cPs) at 8.63 1/s | Viscosity (cPs) at 34.49 1/s | Viscosity (cPs) at 103.45 1/s | Viscosity (cPs) at 206.93 1/s |
|---|---|---|---|---|
| 5 wt % | 502.21 | 238.75 | 86.71 | 45.84 |

Example 7

Effect of pH on the Viscosity of Glucan

Six aliquots of aqueous dispersion of 5 wt % poly alpha-1,3-glucan was prepared as described in Example 1. The pH of aqueous dispersion was 5.5. Two aliquots were adjusted to pH 2.0 and pH 4.0 using 1 N of nitric acid. Three aliquots were adjusted to pH 7.0, pH 9.0 and pH 11.0 using 1 N sodium hydroxide. One aliquot was used without adjusting pH. Viscosity measurements were made as described above. The results summarized in Table 3 indicate that pH has no significant impact on the viscosity of glucan dispersed in water.

TABLE 3

Viscosity of Glucan at Various pH Values

| Poly Alpha-1,3-Glucan Loading | pH | Viscosity (cPs) at 34.49 1/s | Viscosity (cPs) at 103.45 1/s | Viscosity (cPs) at 163.76 1/s | Viscosity (cPs) at 249.98 1/s |
|---|---|---|---|---|---|
| 5 wt % | 2.0 | 188.82 | 69.00 | 46.08 | 32.75 |
| 5 wt % | 4.0 | 207.89 | 76.87 | 51.24 | 36.26 |
| 5 wt % | 5.5 | 238.75 | 86.71 | 56.21 | 39.26 |
| 5 wt % | 7.0 | 217.42 | 80.05 | 53.53 | 37.82 |
| 5 wt % | 9.0 | 206.98 | 78.69 | 52.96 | 37.70 |
| 5 wt % | 11.0 | 212.43 | 80.35 | 54.39 | 38.76 |

Example 8

Effect of Aluminum Chloride on the Viscosity of Glucan

To prepare 5 wt % poly alpha-1,3-glucan dispersion with 15 wt % aluminum chloride, 8.6 g of poly alpha-1,3-glucan wet cake (L6B1C6, 29 wt %) and 7.5 g of aluminum chloride were dispersed in 50 mL of deionized water as described in Example 1 using the homogenization method. 5 wt % poly alpha-1,3-glucan dispersion was prepared as described in Example 6. Viscosity measurements were made, as described in Example 6. The results summarized in Table 4 indicate that the presence of aluminum chloride did not have a significant impact on the viscosity of glucan in water.

TABLE 4

Effect of aluminum chloride on glucan viscosity

| Poly Alpha-1,3-Glucan Loading | Aluminum Chloride Loading | Viscosity (cPs) at 28.20 1/s | Viscosity (cPs) at 105.70 1/s | Viscosity (cPs) at 204.40 1/s |
|---|---|---|---|---|
| 5 wt % | 0 wt % | 63.84 | 21.03 | 12.71 |
| 5 wt % | 15 wt % | 60.51 | 23.55 | 16.47 |

Example 9

Effect of Surfactants on the Viscosity of Glucan

To prepare 5 wt % poly alpha-1,3-glucan dispersion with 2 wt % surfactant, 8.6 g of poly alpha-1,3-glucan wet cake (L6B1C6, 29 wt %) and 1 g of surfactant were dispersed in 50 mL of deionized water, as described in Example 1. Four samples were prepared with four different surfactants, including CTAB (centrimonium bromide), sorbitan monoolate, Tween20 (or polysorbate 20) and Zelec AN (amine neutralized phosphate ester). 5 wt % poly alpha-1,3-glucan dispersion was prepared as described in Example 6. Viscosity measurements were made, as described in Example 6. The results summarized in Table 5 indicate that the presence of surfactant did not have a significant impact on the viscosity of glucan in water.

TABLE 5

Effect of Surfactant on Glucan Viscosity

| Poly Alpha-1,3-Glucan Loading | Surfactant | Viscosity (cPs) at 34.49 1/s | Viscosity (cPs) at 103.45 1/s | Viscosity (cPs) at 163.76 1/s | Viscosity (cPs) at 249.98 1/s |
|---|---|---|---|---|---|
| 5 wt % | 0 wt % | 238.75 | 86.71 | 56.21 | 39.26 |
| 5 wt % | 2 wt % CTAB | 230.58 | 85.65 | 57.83 | 41.33 |
| 5 wt % | 2 wt % Sorbitan monoolate | 218.78 | 78.99 | 54.01 | 38.39 |
| 5 wt % | 2 wt % Tween20 | 193.36 | 68.70 | 46.65 | 33.57 |
| 5 wt % | 2 wt % Zelec AN | 215.6 | 81.11 | 55.16 | 39.45 |

Example 10

Application of Glucan in Personal Care Formulations

To prepare the prototype skin care formulation, (A) and (B) in Table 6 were placed in two separate vessels and were mixed using a propeller stirrer at 75° C. After 5 min, (A) was added to (B) and they were mixed using a propeller stirrer at 75° C. for 1 min. Then (C) was added to the mixture of (A) and (B) at 45° C. During the mixing, the propeller stirrer was set to 500 rpm.

TABLE 6

Skin Care Formulation with Glucan

| Composition | Ingredient | Wt % |
|---|---|---|
| A | Ethylhexyl palmitate (Eastman, emollient) | 15 |
| | Span 60 (Low HLB emulsifier, Croda) | 3 |
| | Tween 60 (High HLB emulsifier, Sigma-Aldrich) | 2 |
| B | Water (Tap) | 63.5 |
| | Propanediol (Humectant, DuPont Tate & Lyle) | 3 |
| | Poly alpha-1,3-glucan (Emulsion stabilizer & aesthetic modifier) | 0.7 |
| | Betaine (Moisturizing agent, Sigma-Aldrich) | 2 |
| C | Propyl paraben (Preservative, Ashland) | 0.8 |

To prepare the prototype acne treatment formulation, (D) and (E) in Table 7 were placed in two separate vessels and were mixed using a propeller stirrer at 75° C. After 5 min, (D) was added to (E) and they were mixed using a propeller stirrer at 75° C. for 1 min. Then (F) was added to the mixture of (D) and (E) at 45° C. During the mixing, the propeller stirrer was set to 500 rpm.

TABLE 7

Acne Treatment Formulation with Glucan

| Composition | Ingredient | Wt % |
|---|---|---|
| D | Ethylhexyl palmitate (Eastman, emollient) | 15 |
|  | Span 60 (Low HLB emulsifier, Croda) | 3 |
|  | Tween 60 (High HLB emulsifier, Sigma-Aldrich) | 2 |
| E | Water (Tap) | 63.5 |
|  | Propanediol (Humectant, DuPont Tart & Lyle) | 3 |
|  | Poly alpha-1,3-glucan (Emulsion stabilizer & aesthetic modifier) | 0.7 |
|  | Salicylic acid (Anti-acne skin treatment, Sigma-Aldrich) | 2 |
| F | Propyl paraben (Preservative, Ashland) | 0.8 |

To prepare the prototype roll-on antiperspirant formulation, (G) and (H) in Table 8 were placed in two separate vessels and were mixed using a propeller stirrer at 75° C. After 5 min, (G) was added to (H) and they were mixed using a propeller stirrer at 75° C. for 1 min. Then (C) was added to the mixture of (G) and (H) at 45° C. During the mixing, the propeller stirrer was set to 500 rpm.

TABLE 8

Roll-on Antiperspirant Formulation with Glucan

| Composition | Ingredient | Wt % |
|---|---|---|
| G | Ethylhexyl palmitate (Eastman, emollient) | 15 |
|  | Span 60 (Low HLB emulsifier, Croda) | 3 |
|  | Tween 60 (High HLB emulsifier, Sigma-Aldrich) | 2 |
| H | Water (Tap) | 50.5 |
|  | Propanediol (Humectant, DuPont Tart & Lyle) | 3 |
|  | Poly alpha-1,3-glucan (Emulsion stabilizer & aesthetic modifier) | 0.7 |
|  | Aluminum chlorohydrate (Active ingredient in deodorant & antiperspirant, Sigma-Aldrich) | 15 |
| I | Propyl paraben (Preservative, Ashland) | 0.8 |

To prepare the prototype hair care formulation, (J) and (K) in Table 9 were placed in two separate vessels and were mixed using a propeller stirrer at 75° C. After 5 min, (J) was added to (K) and they were mixed using a propeller stirrer at 75° C. for 1 min. Then (L) was added to the mixture of (J) and (K) at 45° C. During the mixing, the propeller stirrer was set to 500 rpm.

TABLE 9

Hair Conditioner Formulation with Glucan

| Composition | Ingredient | Wt % |
|---|---|---|
| J | Shea butter ethyl esters (Emollient, AAK) | 2 |
|  | Ceteary alcohol (Waxy thickener, Croda) | 6 |
|  | Tween 60 (High HLB emulsifier, Sigma-Aldrich) | 2 |
| K | Water (Tap) | 76.3 |
|  | Poly alpha-1,3-glucan (Emulsion stabilizer & aesthetic modifier) | 0.7 |
|  | Behentrimonium Chloride (Cationic conditioner, Pilot Chemical) | 2 |
| L | Propyl paraben (Preservative, Ashland) | 1 |

Example 11

Preparation of Hand Lotions

Various hand lotions were prepared for sensory evaluations. The hand lotions were prepared according to the general procedure given below, using the ingredients of TABLE 10.

At room temperature, the ingredients of Phase A were agitated until the mixture was homogeneous. The ingredients of Phase B were combined in a separate vessel and were mixed by hand until homogeneous. The homogeneous composition of Phase B was slowly added to the homogenous mixture of Phase A with stirring. When the addition was complete, the mixture was homogenized by mixing at 5000-9000 revolutions per minute (rpm) for 5-10 minutes. The ingredient of Phase C was then added with stirring to form the desired hand lotions. For Comparative Example B, the pH of the lotion was adjusted to 5.5 by adding a 20 wt % aqueous solution of sodium hydroxide. DI water means deionized water. % Activity means the percentage of ingredient in the composition as added in each example. The Wt % is the weight percentage of the ingredient in the final formulation.

TABLE 10

|  | Ingredient | % Activity | Wt % | Grams |
|---|---|---|---|---|
|  | Phase A | | | |
| Comparative Example A | DI Water | 100 | 74.0 | 296 |
|  | Xanthan Gum | 100 | 0.5 | 2.00 |
|  | Phase B | | | |
|  | Polysorbate 80 | 100 | 2.43 | 9.72 |
|  | Sorbitan Monooleate | 100 | 2.57 | 10.28 |
|  | Mineral Oil | 100 | 20.0 | 80.0 |
|  | Phase C | | | |
|  | GERMABEN ® II | 100 | 0.5 | 2.00 |
|  | Phase A | | | |
| Comparative Example B | DI Water | 100 | 74.0 | 296 |
|  | CARBOPOL ULTREZ ® 10 | 100 | 0.5 | 2.00 |
|  | Phase B | | | |
|  | Polysorbate 80 | 100 | 2.43 | 9.72 |
|  | Sorbitan Monooleate | 100 | 2.57 | 10.28 |
|  | Mineral Oil | 100 | 20.0 | 80.0 |
|  | Phase C | | | |
|  | GERMABEN ® II | 100 | 0.5 | 2.00 |
|  | Phase A | | | |
| Hand Lotion 1 | DI Water | 100 | 69.5 | 163.95 |
|  | Poly alpha-1,3-glucan | 14.92 | 5.00 | 134.05 |
|  | Phase B | | | |
|  | Polysorbate 80 | 100 | 2.43 | 9.72 |
|  | Sorbitan Monooleate | 100 | 2.57 | 10.28 |
|  | Mineral Oil | 100 | 20.0 | 80.0 |
|  | Phase C | | | |
|  | GERMABEN ® II | 100 | 0.5 | 2.00 |
|  | Phase A | | | |
| Hand Lotion 2 | Water | 100 | 73.8 | 283.80 |
|  | Poly alpha-1,3-glucan | 14.92 | 0.50 | 13.40 |
|  | Xanthan Gum | 100 | 0.20 | 0.80 |

TABLE 10-continued

| | Ingredient | % Activity | Wt % | Grams |
|---|---|---|---|---|
| | Phase B | | | |
| | Polysorbate 80 | 100 | 2.43 | 9.72 |
| | Sorbitan Monooleate | 100 | 2.57 | 10.28 |
| | Mineral Oil | 100 | 20.0 | 80.0 |
| | Phase C | | | |
| | GERMABEN ® II | 100 | 0.5 | 2.00 |
| | Phase A | | | |
| Hand Lotion 3 | Water | 100 | 72.0 | 226.57 |
| | Poly alpha-1,3-glucan | 14.00 | 2.50 | 71.43 |
| | Phase B | | | |
| | Polysorbate 80 | 100 | 2.43 | 9.72 |
| | Sorbitan Monooleate | 100 | 2.57 | 10.28 |
| | Mineral Oil | 100 | 20.0 | 80.0 |
| | Phase C | | | |
| | GERMABEN ® II | 100 | 0.5 | 0.5 |

Skinfeel Results: A double-blind, skinfeel analysis was performed according to ASTM E1490-3. The primary attributes evaluated in this study were; rub-out sliminess, afterfeel stickiness, pick-up stringiness and pick-up stickiness. Panelists assessed attributes on a scale from 1-5, where 1 exhibits the least of the attribute and 5 exhibits the most of the attribute. The results are reported in table 11 below as an average value of the panelists' ratings for each attribute. The sum average of these values indicates that the overall sensory experience for the lotions produced with the Poly alpha-1,3-glucans exceed the results of similar lotions produced with either Xanthan Gum or Carbopol Ultrez 10.

TABLE 11

| Attribute | Comparative Example A | Comparative Example B | Hand Lotion 1 | Hand Lotion 2 | Hand Lotion 3 |
|---|---|---|---|---|---|
| Rub-Out Sliminess | 3 | 2 | 2 | 2 | 2 |
| Afterfeel Stickiness | 2 | 3 | 2 | 1 | 1 |
| Pick-Up Stirnginess | 3 | 3 | 2 | 3 | 1 |
| Pick-Up Stickiness | 3 | 2 | 2 | 2 | 2 |
| Sum | 11 | 10 | 8 | 8 | 6 |

Example 12

Application of Glucan in Low Fat Mayonnaise

The low fat mayonnaise was prepared with poly alpha-1,3-glucan by mixing all ingredients in Table 12 using a Silverson homogenizer at 6500 rpm for 5 min. The resulting formulation restored texture of low fat mayonnaise to similar level to full fat product.

TABLE 12

Low Fat Mayonnaise Formulation with Glucan

| Ingredient | Wt % |
|---|---|
| Colzao rape seed oil (Food Ireland) | 30 |
| Poly alpha-1,3-glucan 3% | 50 |
| Xanthan 80 mix (Ingredients Solutions, Inc.) | 0.15 |
| Water (Tap) | 5.55 |
| Vinegar 12% (Ecoshop Direct) | 2.5 |
| Mustard (ShopFoodEx) | 1 |
| Sodium chloride (Sigma-Aldrich) | 0.7 |
| Sucrose (Sigma-Aldrich) | 1 |
| Potassium sorbate (Sigma-Aldrich) | 0.1 |
| Waxy maize starch (Now Foods) | 3.5 |
| Egg Yolk (Honeyville Food Products) | 5.5 |

What is claimed is:

1. A process of preparing a colloidal dispersion, said process comprising:
   (a) providing an aqueous reaction solution comprising sucrose and a glucosyltransferase that synthesizes poly alpha-1,3-glucan, wherein a slurry containing poly alpha-1,3-glucan is produced, and at least 90% of the glycosidic linkages of the poly alpha-1,3-glucan are alpha-1,3-glycosidic linkages;
   (b) filtering the slurry to provide a wet cake of the poly alpha-1,3-glucan, wherein the poly alpha-1,3-glucan is not dried; and
   (c) dispersing the wet cake to provide a colloidal dispersion comprising water and the poly alpha-1,3-glucan, wherein the poly alpha-1,3-glucan of the colloidal dispersion comprises particles with an average diameter of 5 nm to 200 nm.

2. The process of claim 1, further comprising, between steps (b) and (c), washing the wet cake with water.

3. The process of claim 1, wherein at least 95% of the glycosidic linkages of the poly alpha-1,3-glucan are alpha-1,3-glycosidic linkages.

4. The process of claim 3, wherein at least 98% of the glycosidic linkages of the poly alpha-1,3-glucan are alpha-1,3-glycosidic linkages.

5. The process of claim 1, wherein the wet cake contains 60 wt % to 80 wt % water.

6. The process of claim 1, wherein the particles form aggregates with an average diameter of 10 nm to 200 μm.

7. The process of claim 1, wherein the colloidal dispersion comprises 0.1 wt % to 15 wt % poly alpha-1,3-glucan.

8. The process of claim 1, further comprising:
   (d) preparing a personal care product, pharmaceutical product, food product, household product, or industrial product comprising the colloidal dispersion.

9. The process of claim 2, further comprising:
   (d) preparing a personal care product, pharmaceutical product, food product, household product, or industrial product comprising the colloidal dispersion.

10. The process of claim 3, further comprising:
    (d) preparing a personal care product, pharmaceutical product, food product, household product, or industrial product comprising the colloidal dispersion.

11. The process of claim 4, further comprising:
    (d) preparing a personal care product, pharmaceutical product, food product, household product, or industrial product comprising the colloidal dispersion.

12. The process of claim 1, wherein the particles have an average diameter of 10 nm to 100 nm.

13. A process of preparing a colloidal dispersion, said process comprising:

(a) providing a wet cake of poly alpha-1,3-glucan that is not dried, wherein at least 90% of the glycosidic linkages of the poly alpha-1,3-glucan are alpha-1,3-glycosidic linkages, and wherein the poly alpha-1,3-glucan is a product of an aqueous reaction comprising sucrose and a glucosyltransferase that synthesizes poly alpha-1,3-glucan; and (b) dispersing the wet cake to provide a colloidal dispersion comprising water and the poly alpha-1,3-glucan, wherein the poly alpha-1,3-glucan of the colloidal dispersion comprises particles with an average diameter of 5 nm to 200 nm.

14. The process of claim 13, further comprising, between steps (a) and (b), washing the wet cake with water.

15. The process of claim 13, wherein at least 95% of the glycosidic linkages of the poly alpha-1,3-glucan are alpha-1,3-glycosidic linkages.

16. The process of claim 15, wherein at least 98% of the glycosidic linkages of the poly alpha-1,3-glucan are alpha-1,3-glycosidic linkages.

17. The process of claim 13, wherein the wet cake contains 60 wt % to 80 wt % water.

18. The process of claim 13, wherein the colloidal dispersion comprises 0.1 wt % to 15 wt % poly alpha-1,3-glucan.

19. The process of claim 13, further comprising:
(c) preparing a personal care product, pharmaceutical product, food product, household product, or industrial product comprising the colloidal dispersion.

20. The process of claim 14, further comprising:
(c) preparing a personal care product, pharmaceutical product, food product, household product, or industrial product comprising the colloidal dispersion.

21. The process of claim 13, wherein the particles form aggregates with an average diameter of 10 nm to 200 µm.

22. The process of claim 15, further comprising:
(c) preparing a personal care product, pharmaceutical product, food product, household product, or industrial product comprising the colloidal dispersion.

23. The process of claim 16, further comprising:
(c) preparing a personal care product, pharmaceutical product, food product, household product, or industrial product comprising the colloidal dispersion.

24. The process of claim 13, wherein the particles have an average diameter of 10 nm to 100 nm.

* * * * *